United States Patent [19]

Beltramini

[11] Patent Number: 4,661,064

[45] Date of Patent: Apr. 28, 1987

[54] ROTATING TOOL FOR DENTISTRY

[75] Inventor: Giorgio Beltramini, Milan, Italy

[73] Assignee: North Bel S.p.A., Paderne Dugnano, Italy

[21] Appl. No.: 697,119

[22] Filed: Jan. 30, 1985

[30] Foreign Application Priority Data

Feb. 24, 1984 [IT] Italy .............................. 19801 A/84

[51] Int. Cl.⁴ .............................................. A61C 3/06
[52] U.S. Cl. ..................................... 433/166; 29/430;
29/DIG. 7; 29/DIG. 19; 51/206 P
[58] Field of Search .................. 29/401.1, 530, 402.01,
29/527.4, 430, DIG. 7, DIG. 19; 433/165, 166;
51/206 R, 206 P, 395, 357

[56] References Cited

U.S. PATENT DOCUMENTS

| | | | |
|---|---|---|---|
| 2,670,527 | 3/1954 | Roper | 29/402.19 |
| 3,460,292 | 8/1969 | Ferchland | 51/206 R X |
| 3,510,990 | 5/1970 | Steindler | 51/206 R |
| 3,894,339 | 7/1975 | Manzi | 433/166 |
| 4,058,898 | 11/1977 | Nash | 51/206 P X |
| 4,114,322 | 9/1978 | Greenspan | 51/206 R |
| 4,389,192 | 6/1983 | Neuwirth | 433/166 |
| 4,466,795 | 8/1984 | Plischka | 433/166 |

FOREIGN PATENT DOCUMENTS

| | | | |
|---|---|---|---|
| 364490 | 12/1921 | Fed. Rep. of Germany | 51/206 R |
| 237826 | 9/1945 | Switzerland | 51/206 R |
| 379200 | 8/1932 | United Kingdom | 433/165 |

Primary Examiner—Howard N. Goldberg
Assistant Examiner—Ronald S. Wallace
Attorney, Agent, or Firm—Michael J. Striker

[57] ABSTRACT

A rotating tool for use in dentistry, has diamond powder coated areas separated by grooves for enhancing abrasive action, for an improved distribution of cooling and lubricating agent and for easier discharge of waste material.

1 Claim, 9 Drawing Figures

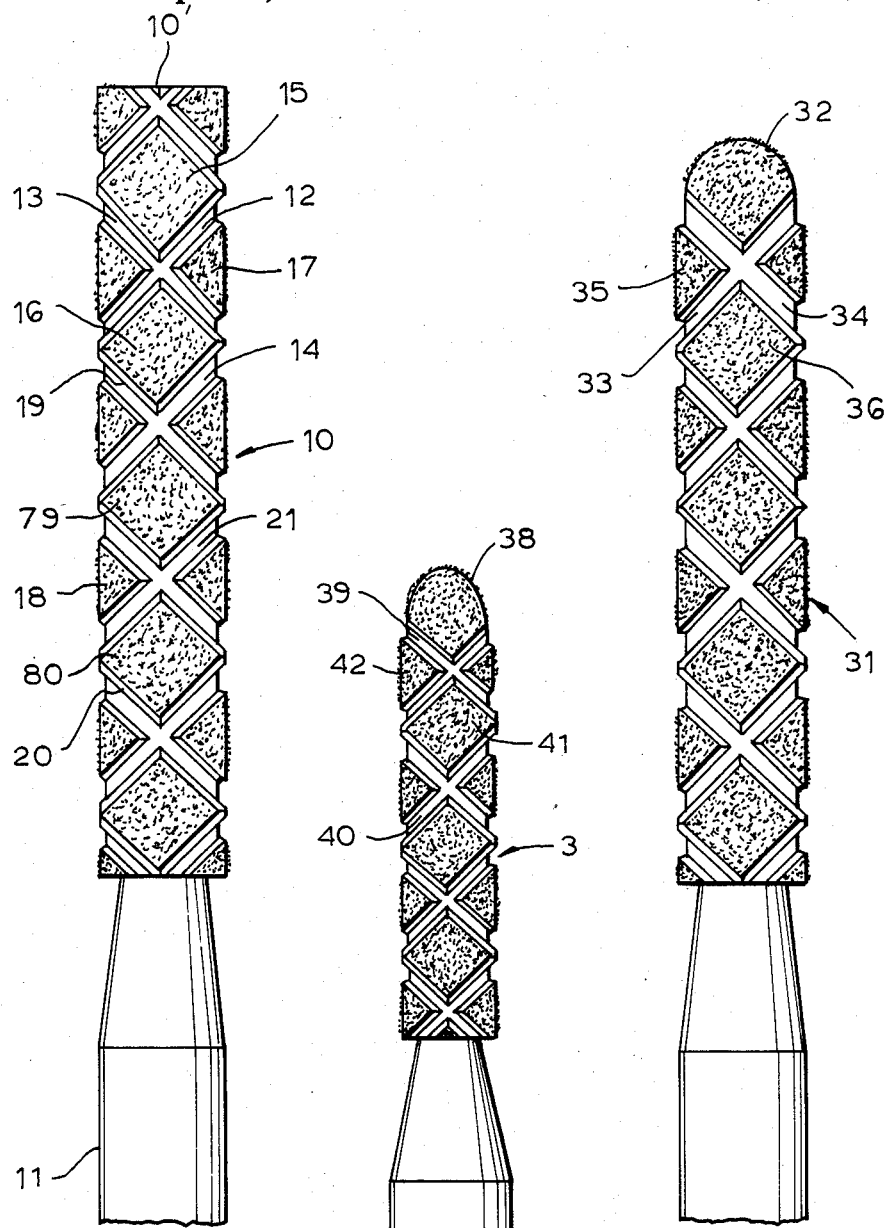

ROTATING TOOL FOR DENTISTRY

BACKGROUND OF THE INVENTION

Well known are rotating tools for industrial and civil uses, especially milling cutters for dentistry, having their working surfaces coated with diamond powder.

Such tools are made using industrial diamond powder applied by electrodeposition, or by other methods, to a surface of various geometrical shapes.

Grains of diamond powder do the work of thousands of single tools, and are found especially useful wherever, as in dentistry, there is a need for high precision, great abrasive power and long life.

Abrasive action naturally depends on the size of the diamond grains, and the tool generally has to work at high pressure on the body being machined. This leads to overheating due to the difficulty of lubricating and cooling liquids to gain access and be able to circulate.

Discharge of waste material is difficult and intermittent.

SUMMARY OF THE INVENTION

The tools subject of this present invention give improved abrasive action at the same time ensuring better cooling, a high capacity for discharging waste material and offering other important advantages as will be explained below.

According to the process, of this present invention, the working surfaces of the tools are designed in areas of different shapes and sizes, separated by grooves and spaces.

The tools may be shaped like cylinders with flat, rounded, ogival or conical heads, or be shaped like a truncated cone with flat, rounded, ogival, flame, wheel, disk or spherical heads, or any other form considered useful.

Formation of the working surface in the areas separated by grooves or spaces is done by pressing, rolling knurling, milling or any other suitable process in accordance with manufacturing and use requirements.

The working surfaces, raised in relation to the grooves and to the spaces, have various geometrical shapes such as cylinders, truncated cones or pyramids, spheres, spherical segments, polyhedrons generally, and other possible or useful shapes.

Said shapes may be the same or different in a single tool.

The grooves and spaces communicate with each other and are continuous, having constant or varied transversal sections according to the shape.

Said grooves and spaces are shaped, sized and disposed in such a way as to ensure optimal distribution of cooling water and of lubricating liquid over the entire working surface of the tool, thus considerably lessening development of heat and also assisting quick and effective discharge of waste material.

The grooves and spaces are preferably made to cross at right angles or at any other angle. The working areas, raised in relation to the grooves and spaces, with angles, especially acute angles as, for example, the rhomboid areas, preferably have the points of said angles lying in the same direction as their forward movement so that abrasive action is enhanced.

The tools generally have a stainless steel base while the diamond powder is applied by electrodeposition or by other suitable methods.

According to the type of execution the grooves and spaces between the raised working areas are smooth, machined, with or without diamond coating.

In order to exclude certain parts of the tool from the diamond coating, said parts like the grooves and intermediate spaces between the raised working areas or even determined areas or grooves or intermediate spaces, are painted, before the diamond coating is applied, with special paints or at any rate with a material such as will prevent deposit and adhesion of the diamond powder.

Characteristics and purposes of the invention will be made even clearer by the following examples of execution illustrated by diagrammatic drawings.

BRIEF DESCRIPTION OF THE DRAWINGS

FIG. 1 is a cylindrical milling cutter;
FIG. 2 is a cylindrical milling cutter with a semi-spherical head;
FIG. 3 is a cylindrical milling cutter with an ogival head.

Figure 9:
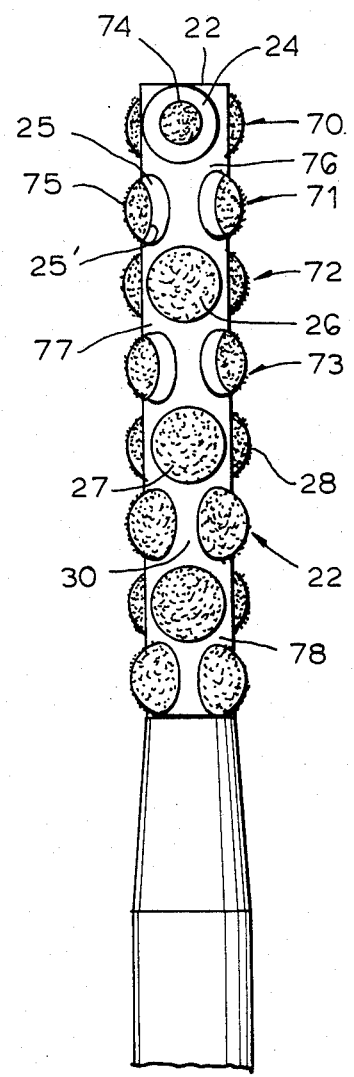

All the cutters in the above figures can have raised working areas consisting of spherical segments or spherical caps surrounded by communicating spaces as in the following figure:

FIG. 9 is a cylindrical cutter with spherical caps and spherical segments.

DETAILED DESCRIPTION OF THE PREFERRED EMBODIMENTS

The milling cutter 10 with a shank 11 and a flat-ended head 10' is made from a stainless steel cylinder in the surface of which crossed grooves have been cut such as 12, 13, 14, 21 which separate the rhomboidal working areas 15, 16, 17, 18. The crossing points of the grooves, and therefore the tips of the rhombs, are aligned parallel to the axis of rotation of the tool.

Due to the effect of the cutter's rotation, edges 19, 20 of the rhombs and especially the tips 79, 80, are the first to encounter the body to be machined and therefore the tool exerts a double action, namely that made by the tip and practically speaking by the whole angular edge of each rhomb and that of abrasion specifically made by the diamond grains, this combined action enhancing the whole effect.

By means of the grooves, cooling water can flow over the entire surface of the cutter, discharging loosened waste material at the same time.

FIG. 2 shows a cylindrical milling cutter 31 with head 32 formed as a spherical cap having grooves 33 and 34 and rhomboidal areas 35, 36.

FIG. 3 illustrates a cylindrical cutter 37 with an ogival head 38, grooves 39 and 40, and rhomboidal areas 41 and 42.

Figures 4, 5, 6:
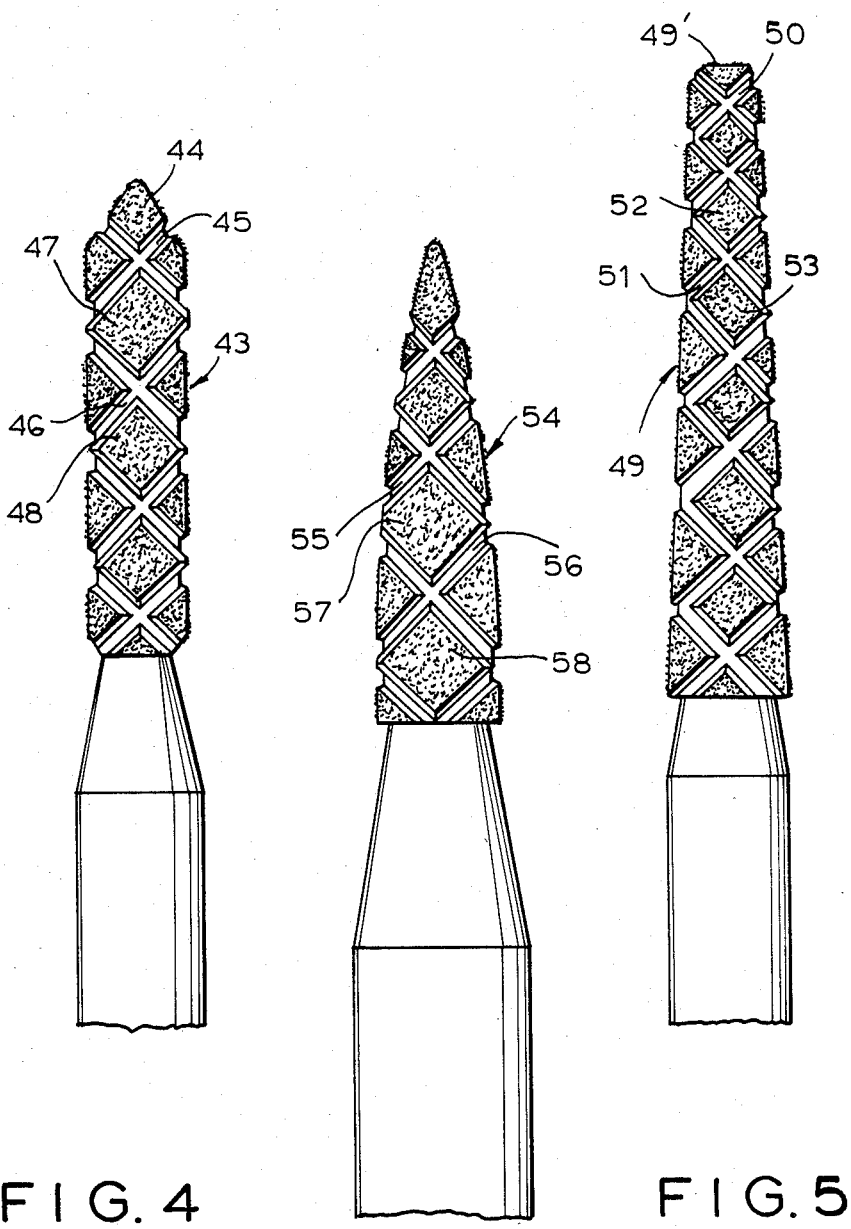
FIG. 4 is a cylindrical milling cutter with a tapering head.
FIG. 5 is a milling cutter shaped as a truncated cone.
FIG. 6 is a flame-shaped milling cutter.

FIG. 4 illustrates a cylindrical cutter 43 with a tapered head 44, grooves 45 and 46, and rhomboidal areas 47 and 48.

FIG. 5 shows a truncated-cone shaped cutter 49 with a flat-ended head 49', grooves 50 and 51, and rhomboidal areas 52 and 53.

FIG. 6 represents a flame-shaped cutter 54, with grooves 55 and 56, and rhomboidal areas 57 and 58.

Figure 7:
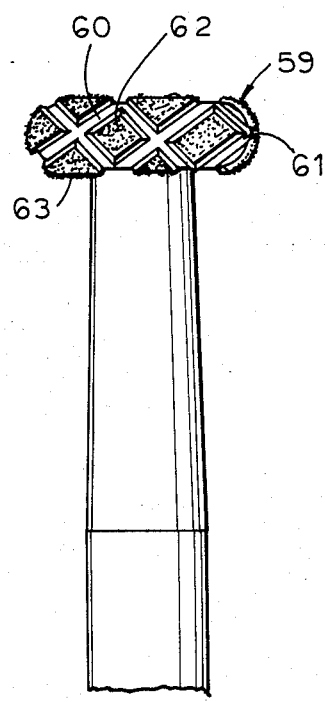
FIG. 7 is a wheel-shaped milling cutter.

FIG. 7 shows a cutter 59 in the form of a small wheel, with grooves 60, 61 and rhomboidal areas 62, 63.

Figure 8:
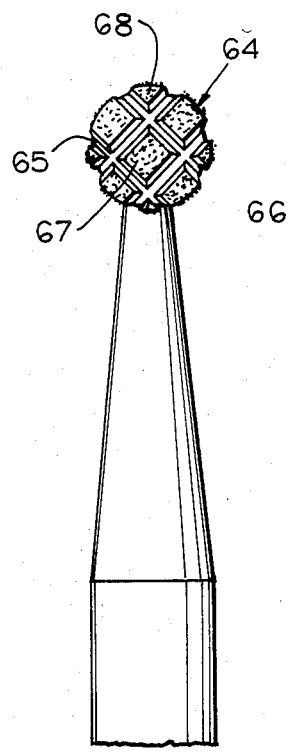
FIG. 8 is a spherical milling cutter.

FIG. 8 illustrates a cutter 64 with a spherical head having grooves 65 and 66 and rhomboidal areas 67 and 68.

All these milling cutters can of course be made with raised areas of practically any shape, even if always separated by grooves more or less like those already described, but also of any other cross section and shape that will ensure an optimum performance according to the various requirements in use.

FIG. 9 shows a cylindrical tool 22 with a flat-ended head 22. The surface of the working part contains various series such as 70, 71, 72, 73 of spherical segments 24, 25 and of spherical caps such as 26, 27, 28 raised above the cylindrical supporting surface 30.

The spherical caps or segments of any one series are placed in an non-aligned position in relation to the series below.

The spherical segments such as 24 and 25 are smooth and have no diamond coating while their raised parts 74 and 75 are diamond coated.

It is clear that the body to be machined will be under severe stress from the circular edges like 25 of the diamond coated base 75, stress that is immediately followed by abrasive action from the diamond grains applied to the base itself thus enhancing overall abrasive effect.

Flow of cooling and lubricating liquid and discharge of loosened material is greatly facilitated by the channels formed by the spaces between the various raised working areas such as 76, 77, 78.

Instead of having rhomboidal raised portions separated by crossed grooves, all the milling cutters of the shapes shown in FIGS. 1 to 8 can of course be made with the spherical caps or spherical segments like the model illustrated in FIG. 9.

The combination of action by the sharp edges of the working areas, raised in relation to the grooves and spaces, with the the specific action of diamond grains, greatly enhances abrasion.

Less pressure is needed by the tool on the body being treated reducing the trauma caused by the removel of material while at the same time increasing effectiveness.

The presence of grooves and spaces between the working areas ensures excellent lubrication and water cooling over the entire working surface greatly reducing development of heat and making sure that loosened material is quickly and completely carried away thus promoting greater efficiency and a higher standard of execution.

The work is done more quickly but at the same time, a better finish, can be achieved while the traumatic effect is lessened especially in the case of dentistry.

As the applications of the invention have been descibed as examples only, not limited to these, it is understood that any equivalent application of the inventive concepts explained and any product executed and/or in operation according to the characteristics of the invention will be covered by its field of protection.

I claim:

1. Diamond-coated milling cutter for dental use, comprising a head and a shank, said head including diamond-coated abrasive zones, and a pair of helicoidal grooves free of diamond coating and of constant cross section, said grooves being identical but set in opposite directions, and extending to a top end of the cutter, a distance between turns of said grooves being considerably greater than the width of said helicoidal grooves, said grooves crossing each other symmetrically and freely so that crossing points form rhomboid-shaped diamond-coated abrasive zones, said grooves procuring a double function of cooling and of removal of waste material, and allowing, for the direction of cutter rotation, conveyance by means of an ascending helicoidal groove of a lubricating and cooling liquid towards a top of the cutter, and removal, by means of a descending helicoidal groove, of waste material from the top towards a lower end of the cutter, the diamond-coated rhomboid-shaped abrasive zones also procuring a double function of cutting away material from a body being treated and of finishing said body, said abrasive zones having edges aligned parallel to the axis of the cutter so as to remove material by a cutting action while by means of the abrasive surfaces the body being treated is finished.

* * * * *